United States Patent
Rubin

(10) Patent No.: US 11,351,132 B2
(45) Date of Patent: *Jun. 7, 2022

(54) ORAL COMBINATION DRUG FORMULATION COMPRISING A NON-STEROIDAL ANTI-INFLAMMATORY DRUG AND A COMPLEMENTARY LOW DOSE OF TRANEXAMIC ACID FOR THE TREATMENT OF MENSTRUAL PAIN ACCOMPANIED WITH EXCESSIVE MENSTRUAL BLOOD LOSS

(71) Applicant: ARSTAT, INC., Flemington, NJ (US)

(72) Inventor: Arkady Rubin, Flemington, NJ (US)

(73) Assignee: Arstat, Inc., Flemington, NJ (US)

( * ) Notice: Subject to any disclaimer, the term of this patent is extended or adjusted under 35 U.S.C. 154(b) by 60 days.

This patent is subject to a terminal disclaimer.

(21) Appl. No.: 16/917,153

(22) Filed: Jun. 30, 2020

(65) Prior Publication Data

US 2020/0330414 A1 Oct. 22, 2020

Related U.S. Application Data

(63) Continuation of application No. 16/696,297, filed on Nov. 26, 2019, now Pat. No. 10,709,679, which is a continuation of application No. 16/292,473, filed on Mar. 5, 2019, now Pat. No. 10,532,037, which is a continuation of application No. 14/051,043, filed on Oct. 10, 2013, now abandoned, which is a continuation of application No. PCT/US2011/060643, filed on Nov. 14, 2011.

(60) Provisional application No. 61/474,392, filed on Apr. 12, 2011.

(51) Int. Cl.
*A61K 31/195* (2006.01)
*A61K 31/192* (2006.01)
*A61K 45/06* (2006.01)

(52) U.S. Cl.
CPC .......... *A61K 31/195* (2013.01); *A61K 31/192* (2013.01); *A61K 45/06* (2013.01)

(58) Field of Classification Search
CPC combination set(s) only.
See application file for complete search history.

(56) References Cited

U.S. PATENT DOCUMENTS

| 7,351,740 | B2 | 4/2008 | Zerangue et al. |
| 2004/0186180 | A1 | 9/2004 | Gelotte et al. |
| 2005/0244495 | A1 | 11/2005 | Moore et al. |
| 2010/0143468 | A1 | 6/2010 | Moore et al. |

OTHER PUBLICATIONS

A Lethaby et al., "Nonsteroidal anti-inflammatory drugs for heavy menstrual bleeding (Review)"; published in The Cochrane Library 2009, pp. 1-55; Issue 1; John Wiley & Sons, Ltd; http://www.thecochranelibrary.com.
A Lethaby et al., "Nonsteroidal anti-inflammatory drugs for heavy menstrual bleeding (Review)"; published online Oct. 17, 2007, the Cochrane Library.
Abstract: Hiroshi Mohri, "High Dose of Tranexamic Acid for Treatment of Severe Menorrhagia in Patients with von Willebrand Disease"; Journal of Thrombosis and Thrombolysis; Springer Netherlands, vol. 14, No. 3, Dec. 2002; accessed Apr. 22, 2010 at http://www.springerlink.com/content/p4804732k3727075.
Abstract: I.S. Fraser et al., "Efficacy of megenamic acid in pateints with a complaint of menorrhagia"; Obstet Gynecol, Nov. 1981; 58(5):543-51; www.ncbi.nlm.nih.gov/pubmed/7029369.
Abstract: Jane Marjoribanks et al., "Nonsteroidal anti-inflammatory drugs for dysmenorrhoea"; Cochrane Database of Systematic Reviews 2010; No. 1. doi 10.1002/14651858.CD001751.pub2.
Abstract: L Makarainen et al., "Primary and myoma-associated menorrhagia: role of prostaglandins and effects of ibuprofen"; Br J Obstet Gynaecol. Sep. 1986; 93(9): 974-8; www.ncbi.nlm.nih.gov/pubmet/3533137.
Abstract: no authors listed, "An evidence-based guideline for the management of heavy menstrual bleeding. Working Party for Guidelines for the Management of Heavy Menstrual Bleeding"; N Z Med. J. May 28, 1999; 112 (1088)174-7; accessed at www.ncbi.nlm.nih.gov/pubmed/10391640.
Abstract: S. Roy et al., "Role of prostaglandins in IUD-associated uterine bleeding—effect of a prostaglandin synthetase inhibitor (ibuprofen)"; Obstre Gynecol Jul. 1981; 58(1): 101-6; www.ncbi.nlm.hih.gov/pubmed/7243136.
American College of Obstetricians and Gynecologists (ACOG), "Practice Bulletin No. 51: Chronic Pelvic Pain"; National Guideline Clearinghouse; Mar. 2004; 103(3): 589-605; Washington, DC.
Andrew M. Kaunitz, "Modern Management of Heavy Menstrual Bleeding"; accessed Sep. 9, 2009.
Andrew S. Coco, "Primary Dysmenorrhea"; American Family Physician, Aug. 1999; 60:489-496; accessed on Jul. 19, 2010 at http://www.aafp.org/afp/990800ap/489.html.
Augusto Caraceni et al., "Pain Measurement Tools and Methods in Clinical Research in Palliative Care: Recommendations of an Expert Working Group of the European Association of Palliative Care"; Journal of Pain and Symptom Management, vol. 23, No. 3, Mar. 2002; 239-255.
Barbara S. Apgar et al., "Treatment of Menorrhagia"; American Family Physician, Jun. 15, 2007; pp. 1813-1819, vol. 75, No. 12.
Center for Drug Evaluation and Research, "Application No. NDA 22-430: Lysteda® Medical Review"; Nov. 10, 2009.

(Continued)

*Primary Examiner* — Jared Barsky
(74) *Attorney, Agent, or Firm* — M&B IP Analysts, LLC

(57) ABSTRACT

A method for relieving menstrual pain and reducing menstrual blood loss in a female is provided. The method comprises administering to the female an oral combination drug formulation comprising a first therapeutically effective dose of a non-steroidal anti-inflammatory drug (NSAID) and a second complementary low dose of tranexamic acid, wherein the NSAID is formulated to relieve the menstrual pain and to reduce a volume of menstrual blood loss of the female, wherein the dose of tranexamic acid ranges from 50 mg to 425 mg per oral combination drug formulation.

13 Claims, No Drawings

(56) References Cited

OTHER PUBLICATIONS

David Chelmow, "Office Gynecology Dilemmas: Nonsurgical options for menorrhagia"; OBG Management, Nov. 2005, pp. 46-53, accessed at www.obgmanagement.com.
Drugs.com: "Ketoprofen Prescribing Information: Official FDA Information, side effects and uses"; accessed Jul. 29, 2010 at http://www.drugs.com/pro/ketoprofen.html.
Drugs.com: "Meclofenamate Prescribing Information: Official FDA Information, side effects and uses"; accessed Jul. 28, 2010 at http://www.drugs.com/pro/meclofenamate.html.
Electronic Medicines Compendium (eMC), "Cyklokapron Tablets—Summary of Product Characteristics (SPC)"; last updated Apr. 5, 2010; accessed Jul. 15, 2010 at http://www.medicines.org.uk/emc/document.aspx?documentID=16512.
Ferring Pharmaceuticals, "Clinical Data Demonstrates the LYSTEDA Significantly Reduced Menstrual Blood Loss and Limitations on Social, Leisure and Physical Activities in Women With Cyclic HMB"; PR Newswire; accessed Jul. 15, 2010 at http://prnewswire.com.
Haymarket Medical Education, "Heavy Menstrual Bleeding: Assessing Impact, Evaluating Management Options"; Oct. 2009; Supplement to OBG Management; Boston University School of Medicine, Boston, MA (US).
International Searching Authority, "International Search Report for International Patent Application No. PCT/US11/60643"; dated Mar. 26, 2012.
International Searching Authority, "Patent Cooperation Treaty (PCT) Written Opinion of the International Searching Authority, for corresponding International Patent Application No. PCT/US11/60643"; dated Mar. 26, 2012.
John Bonnar et al., "Treatment of menorrhagia during menstruation: randomised controlled trial of ethamsylate, mefenamic acid, and tranexamic acid"; BMJ vol. 313, Sep. 7, 1996; pp. 579-582; Dublin Ireland.
Joseph S. Sanfilippo et al., "Update: Options in Endometrial Ablation"; Supplement to OBG Management, Dec. 2009; Dowden Health Media; www.obgmanagement.com.
Joseph Y. Lee, et al., "Treatment of Menorrhagia with Tranexamic Acid"; J Soc Obstet Gynaecol Can 2000; Oct. 2000; vol. 22(10): pp. 794-798; Kingston, Ontario (CA).
Ken Muse et al., "Effect of Baseline Menstrual Blood Loss or BMI on Menorrhagia Treated with a Novel Tranexamic Acid"; presented at American College of Obstetricians and Gynecologists (ACOG) Annual Meeting May 17, 2010.
Kirsten Duckitt et al., "BMJ Clinical Evidence: Menorrhagia"; Search date Oct. 2007; BMJ Clinical Evidence 2008; 09:805; BMJ Publishing Group Ltd. 2008; pp. 1-23.
Linda French, "Dysmenorrhea"; American Family Physician, Jan. 15, 2005; 71(2): pp. 285-291; accessed on Jul. 26, 2010 at http://www.aafp.org/afp/2005/0115/p285.html.
M. K. Oehler, "Menorrhagia: an update"; Acta Obstetricia et Gynecologica Scandinavica 2003; 82: 405-422; Denmark.
Medscape, "Ibuprofen Oral: Dosage, Uses and Warnings"; accessed Jul. 29, 2010 at http://www.medscape.com/druginfo/dosage?drugid=5166&drugname=Ibuprofen+Oral&monotype=default.
Merck & Co. Inc., "MerckMedicus Modules: Dysmenorrhea—Epidemiology"; last updated: Dec. 2001; accessed on Jul. 25, 2010 at http://www.merckmedicus.com/pp/us/hcp/diseasemodules/dysmenorrhea/epidemiology.jsp.
Michelle L. Proctor et al., "BMJ Clinical Evidence: Dysmenorrhea"; Search date Jul. 2006; 03:813; BMJ Publishing Group Ltd. 2007.
Monash University, "International Women's Health Update: Management Options: Antifibrinolytics"; last updated Aug. 15, 2006; accessed at www.med.monash.edu.au/ob-gyn/research/mangement.html.
National Collaborating Centre for Women's and Children's Health, "Heavy menstrual bleeding: Clinical Guideline"; Jan. 2007; pp. i-45, RCOG Press: London (UK).
Novartis Pharmaceuticals Corp., "Cataflam® (diclofenac potassium immediate-release tablets) Prescribing Information"; Feb. 25, 2009 Novartis Pharmaceuticals Corporation; East Hanover, NJ (US).
Olavi Ylikorkala et al., "Comparison between antifibrinolytic and antiprostaglandin treatment in the reduction of increased menstrual blood loss in women with intrauterine contraceptive devices"; British Journal of Obstetrics and Gynaecology, Jan. 1983, vol. 90, pp. 78-83.
Pharmacia & Upjohn, "Motrin® Ibuprofen tablets, USP"; Full Prescribing Information; revised Jul. 2003; Pharmacia & Upjohn Co.; Kalamazoo, MI (US).
Roche Laboratories, Inc., "Naprosyn® (naproxen tablets) Prescribing Information"; Revised: Sep. 2007; Roche Laboratories Inc.; Nutley, NJ (US).
Ronald T. Burkman et al., "Noncontraceptive Health Benefits of Progestin-Only Contraceptive Agents"; The Female Pateint, Aug. 2008; accessed on Jul. 16, 2010 at http://www.femalepatient.com/html/cme/articles/033_08_047.asp.
Sciele Pharma, Inc., "Ponstel® (Mefenamic Acid Capsules, USP) Medication Guide"; Effective Date Feb. 19, 2008; Sciele Pharma, Inc.; Atlanta, GA (US).
Society of Obstetricians and Gynaecologists of Canada (SOGC) Clinical Practice Guideline, "Primary Dysmenorrhea Consensus Guideline"; Journal of Obstetricians and Gynaecologists of Canada (JOGC) Dec. 2005, No. 169, pp. 119-1120.
Subramanian Natesan et al., "Improved Rp-Hplc Method for the Simultaneous Estimation of Tranexamic Acid and Mefenamic Acid in Tablet Dosage Form"; Pharmaceutica Analytica Acta, Feb. 20, 2011, vol. 2, Iss 1, p. 1-6, entire document, esp. p. 1, para 3.
The European Agency for the Evaluation of Medicinal Products, Committee for Proprietary Medicinal Products (CPMP), "Opinion Following an Article 10 Referral—CYKLO-f"; Jul. 27, 2000; EMEA, 2000: London (UK).
University of Texas at Austin School of Nursing, Family Practitioner Program, "Recommendations for the Treatment of Dysmenorrhea"; 2000. National Guideline Clearinghouse; accessed Jul. 21, 2010 at http://www.guideline.gov/guidelines/ngc_1963.html.
W.Y. Zhang et al., "Efficacy of minor analgesics in primary dysmenorrhoea: a systematic review"; British Journal of Obstetrics and Gynaecology; Jul. 1998; vol. 105, pp. 780-789; Nottingham, UK.
Xanodyne Pharmaceuticals, Inc., "Lysteda®. Full Prescribing Information"; Issued: Nov. 2009; Newport, KY (US).
Yusoff M. Dawood, "Dysmenorrhea"; The Global Library of Women's Medicine, last updated Jun. 2008; DOI 10.3843/GLOWM.10009.

ORAL COMBINATION DRUG FORMULATION COMPRISING A NON-STEROIDAL ANTI-INFLAMMATORY DRUG AND A COMPLEMENTARY LOW DOSE OF TRANEXAMIC ACID FOR THE TREATMENT OF MENSTRUAL PAIN ACCOMPANIED WITH EXCESSIVE MENSTRUAL BLOOD LOSS

CROSS REFERENCE TO RELATED APPLICATIONS

This application is a Continuation of U.S. patent application Ser. No. 16/696,297 filed Nov. 26, 2019, now allowed. The application Ser. No. 16/696,297 is a Continuation of U.S. patent application Ser. No. 16/292,473 filed Mar. 5, 2019, now U.S. Pat. No. 10,532,037, which is a Continuation of U.S. patent application Ser. No. 14/051,043 filed Oct. 10, 2013 which is a Continuation of international application PCT/US2011/060643 filed on Nov. 14, 2011, which claims the benefit of U.S. provisional patent application No. 61/474,392 filed on Apr. 12, 2011, the contents of which are incorporated by reference in their entirety.

TECHNICAL FIELD

The present invention relates to the treatment of female menstrual disorders. More specifically, the present invention relates to the pharmacological treatment of menstrual pain accompanied with excessive menstrual blood loss. Further, the present invention relates to the pharmacological treatment of menstrual pain accompanied with excessive menstrual blood loss by administration of an oral combination drug formulation comprising a non-steroidal anti-inflammatory drug (NSAID) and a complementary low dose of tranexamic acid.

BACKGROUND

Menstrual disorders affect the lives of millions of women. Painful menstrual periods associated with heavy menstrual bleeding often require medical attention and initiation of appropriate therapy.

Painful menstrual periods may be clinically diagnosed as primary or secondary dysmenorrhea. Primary dysmenorrhea is defined as painful menstrual periods in women with normal pelvic anatomy. It is characterized by crampy pelvic pain beginning shortly before or at the onset of menstrual periods and lasting one to three days. Dysmenorrhea also may be secondary to pelvic organ pathology.[1] Reported dysmenorrhea prevalence rates range from 43% to 90%. The variability of these estimates is explained by differences in the methods of data collection, the definitions of dysmenorrhea and populations studied[2].

Heavy menstrual bleeding is defined as menorrhagia when the menstrual blood loss (MBL) exceeds 80 mL per menstrual cycle. In real-world practice, if a woman's periods are so heavy or so long that she finds them distressing, then she is experiencing heavy menstrual bleeding. One-third of all women report heavy menstrual bleeding at some point in their lives, and in Western countries about 5% of reproductive-aged women seek treatment for it annually[3].

With the high prevalence of dysmenorrhea and menorrhagia, one may expect that a substantial number of women suffer from both diseases concomitantly. Days of painful menstrual periods in conjunction with excessive MBL may also be experienced by women not clinically diagnosed with either condition, or diagnosed with only one of them (e.g., clinically diagnosed menorrhagia in the absence of dysmenorrhea; or clinically diagnosed dysmenorrhea in the absence of menorrhagia).

In North America and Europe, dysmenorrhea and menorrhagia are often treated by off-label use of approved hormonal contraceptives. For a number of women, the treatments may not be acceptable due to known contraindications, hormone-related adverse events and/or undesirable changes in the menstrual bleeding pattern, including unpredictable intra-cyclic bleeding, irregular menstrual periods and/or the development of amenorrhea[4,5,6] Due to known safety issues, danazol is rarely considered as a viable pharmacological treatment option. Surgical removal of the uterus (i.e., hysterectomy) may be considered for women with severe, refractory dysmenorrhea and menorrhagia. Yet, this is a radical treatment option with known undesirable consequences, including loss of fertility, surgical morbidity, as well as entailing high cost. There is limited evidence supporting minimally invasive methods of endometrial destruction as efficacious treatment options for dysmenorrhea and menorrhagia[1,7].

Non-steroidal anti-inflammatory drugs (NSAIDs) are currently considered the most appropriate initial therapy for dysmenorrhea.[1,8,9,10,11,12,13,14,15,16] The following NSAIDs are commonly prescribed for the treatment of pain associated with dysmenorrhea: (1) Mefenamic acid, (Ponstel®); (2) Ibuprofen (Motrin®, Advil®); (3) Diclofenac potassium (Cataflam®; (4) Naproxen sodium (ANAPROX®/ANAPROX® DS); (5) Ketoprofen (Orudis®); (6) Meclofenamate sodium.[17,18,19,20,21,22,23] Ibuprofen, naproxen and ketoprofen are recommended drugs.[11,12] In the published meta-analysis, ibuprofen was singled out as the drug having the most favorable risk-benefit ratio.[16]

Oral NSAIDs have been shown to reduce MBL.[6,25,26] The NSAIDs' ability to reduce MBL is related to the established relationship of endomyometrial prostaglandins to the genesis of menorrhagia. The most extensively studied NSAIDs, the fenamates, inhibit prostaglandin synthesis and bind to prostaglandin receptors which are significantly increased in women with menorrhagia.[24]

However, many patients desire greater reduction of the amount of menstrual flow than what is typically achievable using recommended doses of oral NSAIDs.[29] To ensure greater reduction of MBL, the maximal NSAID doses must often be administered.[4] This leads to undesirable side effects such as diarrhea, nausea, vomiting, stomach pain, constipation, and allergic reactions and is not optimal, particularly if a much lower NSAID dose is sufficient to alleviate menstrual pain. As an example, a high dose of ibuprofen (800 mg every 8 hours) has been recommended for MBL reduction[5], while a lower dose (400 mg every 4 hours as necessary for pain relief[19]) may be sufficient to alleviate menstrual pain. A recommendation in the FDA-approved class labeling for NSAIDs is to use the lowest effective dose for the shortest duration possible.[21]

In addition, NSAIDs demonstrate inferior efficacy in reducing MBL when compared to another drug widely used for treatment of menorrhagia, oral tranexamic acid. Oral tranexamic acid is marketed in the U.S. as Lysteda® and both within and outside the U.S. as Cyklokapron®. As is reported in the Lysteda label, tranexamic acid is a synthetic lysine amino acid derivative which diminishes the dissolution of hemostatic fibrin by plasmin. In the presence of tranexamic acid, the lysine receptor binding sites of plasmin for fibrin are occupied, preventing binding to fibrin monomers, thus preserving and stabilizing fibrin's matrix structure.[32] The antifibrinolytic activity of tranexamic acid results in inhibition of the dissolution of clots.[28] For many women, oral tranexamic acid is an efficacious treatment option. Clinical studies indicated that a 3900 mg/day regimen (marketed in the US as Lysteda) meets MBL reduction targets established by the FDA and significantly reduces limitations on social, leisure and physical activities.[32,36]

However, the treatment-induced changes in MBL established in the Lysteda clinical trials may be not satisfactory for some women, and many patients may desire even greater reduction of the amount of menstrual flow. As was noted in the medical review of the Lysteda NDA, less than half (44%) of subjects returned to normal MBL after treatment (i.e., achieved a mean on-treatment MBL of less than 80 mL). There were no statistically significant differences between tranexamic acid and placebo treatment with regard to reduction of large stains, small and large clots as well as for changes in serum ferritin levels.[36] The latter endpoint is particularly meaningful for women with impaired iron status and/or clinically-diagnosed anemia frequently associated with menorrhagia.

In the evaluation of tranexamic acid in the treatment of menorrhagia performed in 2000 by the European Agency for the Evaluation of Medicinal Products (EMEA), a dose-dependent increase in efficacy was noted. The same review recommended a daily dose of 3-4 g/day and indicated that the risk of gastrointestinal adverse events is increased at 6 g/day.[34] While the FDA-approved Lysteda regimen (up to 3.9 g/day) is within the aforementioned recommended dosing range, certain Warnings and Precautions, including dose adjustment in women with renal impairment; increase in the risk of blood clots, stroke, or myocardial infarction in the event of concomitant therapy with hormonal contraceptives; the possibility of severe allergic reactions; and visual or ocular adverse effects,[6] reflect regulatory concerns regarding Lysteda's safety. In the risk-benefit assessment, the FDA medical reviewer suggested a 50% dose reduction for women who do not tolerate the common adverse events associated with the approved treatment regimen.[36]

A possibility of combining oral NSAID and oral tranexamic acid treatments has been suggested.[6] It may be assumed that the currently-approved doses of 3.9 mg/day for Lysteda (US) and 3.0 mg/day for Cyklokapron® (ex-US) would be used.[27,29] A combination oral tablet containing the standard doses of tranexamic acid (500 mg) and NSAID mefenamic acid (250 mg) is marketed in India (under Gynameno-Plus® and other trade names). For the treatment of primary dysmenorrhea, the mefenamic acid (Ponstel®) label recommends 500 mg as an initial dose followed by 250 mg every 6 hours, starting with the onset of bleeding and associated symptoms.[17] To comply with this recommendation, five Gynameno-Plus tablets must be taken daily. Therefore, the daily dose of co-administered tranexamic acid would be 2500 mg (i.e. 65% and 85% of Lysteda and Cyklokapron approved doses, respectively). These treatment modalities do not take into consideration the substantial contribution of the NSAID component to the MBL reduction. As a result, they use doses of tranexamic acid which are much greater than needed for adequate control of excessive MBL resulting in increased incidence of adverse events.

Taken together, the clinical evidence indicates that the efficacy of oral NSAIDs in the treatment of dysmenorrhea accompanied with heavy menstrual bleeding cannot ensure adequate reduction of MBL. Due to safety issues reflected in relevant FDA guidance, an increase in an NSAID dose cannot be considered as an acceptable option. The efficacy of oral tranexamic acid in the reduction of MBL must also be weighed against the potentially disturbing side effects associated with this medication. When administered concomitantly via the conventional oral route at approved doses, the combination of an NSAID and tranexamic acid may raise safety concerns.

SUMMARY

The present invention provides a method for effectively relieving menstrual pain and reducing excessive menstrual blood loss (MBL) without the undesirable side effects of currently recommended doses for oral medications by providing for an oral combination drug formulation comprising (i) a first therapeutically effective dose of a non-steroidal anti-inflammatory drug (NSAID), wherein said NSAID is able to reduce the volume of MBL, and (ii) a second complementary low dose of tranexamic acid. In a preferred embodiment, the dose of tranexamic acid is in the range from 50 mg to 425 mg per oral combination drug formulation. In the most preferred embodiment, the dose of tranexamic acid is in the range from 150 mg to 250 mg per oral combination drug formulation.

The present invention takes advantage of the ability of certain NSAIDs to reduce excessive MBL and of the different mechanisms of action between NSAIDs and tranexamic acid in MBL reduction, and allows for the use of lower doses of tranexamic acid as compared to those currently employed. Due to the combining of MBL-reducing NSAIDs with tranexamic acid, the present invention also avoids the need to increase the doses of NSAIDs above doses which are efficacious for pain relief.

As compared to the currently available treatments, oral combination drug formulations of the present invention provide increased efficacy in the reduction of MBL in women suffering from painful menstrual periods accompanied by excessive MBL.

According to the present invention, an effective MBL reduction is achievable with a relatively low complementary daily dose of tranexamic acid, ranging from 10% to 55%, preferably ranging from 10% to 33% of the currently used oral dose of tranexamic acid (marketed in the US as Lysteda®). According to the present invention, a complementary dose of up to 2125 mg daily, preferably up to 1300 mg daily, most preferably ranging from 600 mg to 1000 mg daily (as opposed to the Lysteda's 3900 mg/day dose), is used for desirable MBL reduction.

According to the present invention, the dose of the selected NSAID and tranexamic acid takes into account the efficacy of the given NSAID in reducing the volume of MBL. For NSAIDs which cause reduction in the volume of MBL, the dose of co-administered tranexamic acid can be substantially lowered. Different mechanisms of the MBL-reducing action (e.g., inhibition of prostaglandin synthesis and binding to prostaglandin receptors by NSAID; reduction of plasminogen activator and plasmin levels by tranexamic acid) result in at least an additive effect of the two components of the oral combination drug formulations of the present invention. The appreciable contribution of the NSAID component to the MBL reduction dictates the selection of both NSAID and tranexamic acid doses. In addition, the relative severity of menstrual pain and the amount of MBL in the target population must also be taken into account. For example, in women with severe dysmenorrhea and relatively modest MBL, addition of a very small dose of tranexamic acid to the potent dose of NSAID should be considered. If, however, menstrual pain is less than severe and the volume of MBL is high, then a relatively small dose of NSAID is combined with a slightly greater complementary dose of tranexamic acid. In any case, the goal is an effective treatment of both conditions with an appropriate dose of each component. The method of the present invention ensures achievement of the clinical targets established in the treatment of menstrual pain and excessive MBL.

The critical aspect of the method of the present invention is the use of a complementary low dose of tranexamic acid. Data from the Lysteda® clinical program suggests 40% as a desirable treatment-induced decrease in the MBL.[36] An approximate 40% decrease in MBL was also considered as clinically relevant in the scientific evaluation of tranexamic acid in the treatment of menorrhagia performed in 2000 by the European Agency for the Evaluation of Medicinal Products, EMEA. The same review indicated a dose-dependent increase of efficacy of tranexamic acid.[34] The dose-dependent percent decrease in MBL is supported by the Lysteda clinical data: a mean percent change in MBL for 1950 mg/day regimen was approximately 25% vs. 39% for the 3900 mg/day dose.[36]

Across a number of evaluated studies, an overall mean percent reduction in MBL for NSAIDs was close to 30%.[27] Therefore, an additional 10% decrease in MBL may be considered as an appropriate target for the complementary dose of tranexamic acid. Assuming proportionality across the entire tranexamic acid dose range, it may be hypothesized that up to 1000 mg of tranexamic acid daily may be sufficient to achieve this target. To accommodate the possibility of a less-than-expected effect of NSAID on the MBL, the more conservative estimate would be a complementary dose of up to 1300 mg/day, or 33% of the currently used Lysteda dose. To ensure additional reduction of the severe menstrual blood loss (MBL), the most conservative estimate would be a complementary dose of up to 2125 mg/day, or 55% of the currently used Lysteda dose.

The MBL reduction targets must be adjusted for females suffering from both menstrual pain and excessive MBL when the latter alone would not be clinically diagnosed as menorrhagia. The data from the Lysteda clinical program suggests 25% as an adequate treatment-induced decrease in the MBL in women with excessive MBL when pretreatment (baseline) MBL is relatively modest (less than 100 mL per menstrual cycle).[38] Such a percent decrease in MBL should be adequate for women with no clinical diagnosis related to menorrhagia and would allow for a lower complementary dose of tranexamic acid (possibly, up to 10%-15% of the daily dose of Lysteda).

Specific examples of the calculation of complementary doses of tranexamic acid for individual NSAIDs (based on historical data) are presented in one of the following sections.

While the exact useful doses for each drug in the method of the invention are going to be determined in clinical trials, the possibility of a substantial dose decrease, relative to the currently employed doses of oral tranexamic acid, is surprising and new. Also surprising and new is the possibility of reduced doses of an NSAID when compared to the doses recommended for women with painful menstrual periods accompanied with excessive MBL: either no NSAID dose increase is needed, or a smaller NSAID dose increase is needed according to the present invention to ensure adequate MBL reduction in addition to effective pain relief.

While the optimal treatment duration will be determined during clinical trials, it is expected that the drug administration must start at the onset of the menstrual period and last for several days, until the end of the menstrual period or at least until the end of painful and/or heavy menstrual bleeding.

Reduced oral doses of NSAID and tranexamic acid used according to the present invention should lead to a lower incidence of adverse events, such as diarrhea, nausea, vomiting, stomach pain, upset stomach, constipation, heartburn, allergic reactions, disturbance of color, sharpness, or field of vision, etc. The reduced complementary dose of tranexamic acid may also eliminate the risks of systemic toxicity and thromboembolism associated with its oral administration.

The oral combination drug formulations of the present invention allows practitioners to achieve high efficacy in the management of menstrual pain accompanied with excessive MBL, and a decrease in drug-related adverse events, as well as the convenience of a single drug formulation.

DETAILED DESCRIPTION

The embodiments disclosed herein are only examples of the many possible advantageous uses and implementations of the innovative teachings presented herein. In general, statements made in the specification of the present application do not necessarily limit any of the various claimed embodiments. Moreover, some statements may apply to some inventive features but not to others.

Definitions

Menstrual flow is defined as encompassing menstrual blood and/or menstrual fluid.

Menstrual pain relief is defined as a decrease in the severity of menstrual pain when compared to the pre-treatment conditions. Menstrual pain relief may be complete (when a woman does not experience any pain) or partial (when a woman experiences less severe pain).

A therapeutically effective dose/amount of NSAID is defined as the amount of oral NSAID that results in significant (at least, 20%) changes in a 4-point verbal rating scale ranging from 0 (no pain) to 3 (severe pain) and/or the 100-mm visual analog scale of severity of the menstrual pain (see reference 43), when compared to the pre-treatment conditions.

A therapeutically effective dose/amount of tranexamic acid is defined as the amount of the drug that results in a significant (at least, 10%) change in the volume of menstrual blood loss (MBL) when compared to the pre-treatment conditions.

Certain disclosed embodiments provide a method for relieving menstrual pain and reducing menstrual blood loss (MBL) in a female by administering to the female an oral combination drug formulation comprising a first therapeutically effective dose of a non-steroidal anti-inflammatory drug (NSAID), wherein said NSAID is able to reduce the volume of MBL, and a second complementary low dose of tranexamic acid. In one embodiment, the dose of tranexamic acid is in the range from 50 mg to 425 mg, most preferably from 150 mg to 250 mg, per oral combination drug formulation. In a further embodiment, total daily dose of tranexamic acid does not exceed 2125 mg. In yet another embodiment, the total daily dose of tranexamic acid does not exceed 1300 mg, and is most preferably ranging from 600 mg to 1000 mg.

In one embodiment, the oral combination drug formulation of the present invention can be administered to females, e.g., one to six times per day. In a further embodiment, the oral combination drug formulation of the invention can be administered to females suffering from menstrual pain accompanied with excessive MBL, from the onset of menstrual bleeding until the resolution of related symptoms or the end of the menstrual period.

In one embodiment, non-limiting examples of useful oral drug formulations useful in the method of the present invention include oral tablet, oral capsule and oral caplet. In another embodiment, NSAIDs useful in the formulations of the present invention have proven analgesic efficacy and/or an indication for the treatment of menstrual pain and are also be able to reduce the volume of MBL. Non-limiting examples of useful NSAIDs include, e.g., ibuprofen, naproxen, diclofenac, ketoprofen, mefenamic acid, and metabolites thereof.

In one embodiment, NSAID doses range from 5 mg to 1000 mg per oral combination drug formulation. In a further embodiment, the NSAID is ibuprofen. Preferably, the dose of ibuprofen ranges from 100 mg to 800 mg per oral combination drug formulation. In another embodiment, the NSAID is naproxen. Preferably, the dose of naproxen ranges from 150 mg to 600 mg per oral combination drug formulation. In yet another embodiment, the NSAID is diclofenac. Preferably, the dose of diclofenac is ranges from 5 mg to 50 mg per oral combination drug formulation. In a further embodiment, the NSAID is ketoprofen. Preferably, the dose of ketoprofen ranges from 5 mg to 50 mg per oral combination drug formulation. In another embodiment, the NSAID is mefenamic acid. Preferably, the dose of mefenamic acid ranges from 50 mg to 500 mg per oral combination drug formulation.

In one embodiment, the method of the invention is used to treat females clinically diagnosed with primary dysmenorrhea. In another embodiment, the method of the invention is used to treat females clinically diagnosed with secondary dysmenorrhea. In yet another embodiment, the method of the invention is used to treat females with no clinical diagnosis related to primary dysmenorrhea or secondary dysmenorrhea, but who perceive their menstrual periods to be painful. In a further embodiment, the method of the invention is used to treat females with menstrual bleeding of less than 80 mL per menstrual cycle. In another embodiment, the method of the invention is used to treat females with menstrual bleeding of more than 80 mL per menstrual cycle.

In one embodiment, the method of the invention is used to treat females clinically diagnosed with menorrhagia. In another embodiment, the method of the invention is used to treat females clinically diagnosed with idiopathic menorrhagia. In a further embodiment, the method of the invention is used to treat females clinically diagnosed with cyclic heavy menstrual bleeding. In yet another embodiment, the method of the invention is used to treat females clinically diagnosed with dysfunctional uterine bleeding. In a further embodiment, the method of the invention is used to treat females with no clinical diagnosis related to menorrhagia, idiopathic menorrhagia, cyclic heavy menstrual bleeding, or dysfunctional uterine bleeding, but who perceive their menstrual periods to be heavy. In yet another embodiment, the method of the invention is used to treat females clinically diagnosed with anemia.

In one embodiment, an oral combination drug formulation consists of 400 mg ibuprofen and 150-200 mg of tranexamic acid; this oral combination drug formulation is administered four times daily to treat females clinically diagnosed with primary or secondary dysmenorrhea and clinically diagnosed with menorrhagia. In another embodiment, an oral combination drug formulation consists of 200 mg ibuprofen and 200-250 mg tranexamic acid; this oral combination drug formulation is administered three times daily to treat females with no clinical diagnosis related to primary dysmenorrhea or secondary dysmenorrhea and with no clinical diagnosis related to menorrhagia.

The active compounds of the present invention can be formulated in an oral combination drug formulation in combination with one or more pharmaceutically acceptable carriers and/or excipients such as, e.g., stabilizers, lubricants, diluents, flavorants, colorants, buffers, and disintegrants. Suitable pharmaceutically acceptable carriers include any and all conventional solvents (such as, e.g., water, physiological solution, dextrose, glycerol, ethanol, and the like, as well as combinations thereof), wetting agents, emulgators, buffers, conservants, antioxidants, dispersion media, fillers, solid carriers, coatings, antibacterial and antifungal agents, isotonic and absorption delaying agents, as well as other well-known agents which enhance the shelf life or effectiveness of one or more of the active components of the composition. Examples of such useful substances can be found e.g. in the book Remington: The Science and Practice of Pharmacy. Lippincott Williams & Wilkins 2005. Except insofar as any conventional media or agent is incompatible with the active ingredients, use thereof in compositions of the present invention is contemplated.

Oral combination drug formulations of this invention may be formulated to modify and control the distribution of the NSAID and/or tranexamic acid present in a composition upon administration to the female; such controlled release formulations are well known and widely practiced in the art. In particular, the controlled release formulation may be an extended release formulation, which can reduce the required frequency of administration by maintaining the concentration of the active substances in the composition at desired levels. Any suitable extended release delivery system may be used. Some exemplary methods and technologies useful for implementing controlled release pharmaceutical formulations, and particularly extended-release formulations, are discussed in the following publications: Chasin M, Langer R S Biodegradable Polymers as Drug Delivery Systems. New York: M. Dekker 1990; Park K et al. Biodegradable Hydrogels for Drug Delivery. Lancaster, Pa.: Technomic Pub 1993; Wise D L Handbook of Pharmaceutical Controlled Release Technology. New York: Marcel Dekker 2000; Li X P, Jasti B R Design of Controlled Release Drug Delivery Systems. New York: McGraw-Hill 2006; Benita S Microencapsulation: Methods and Industrial Applications. New York: Taylor & Francis 2006; and Rathbone M J Modified-Release Drug Delivery Technology. New York: Informa Healthcare 2008.

It will be readily evident to the one skilled in the art that the various approaches useful in preparing pharmaceutical formulations, as described herein, and other approaches known in the art, may be usefully combined in a single oral combination drug formulation.

The present invention is also described and demonstrated by way of the following non-limiting examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Determination of a complementary dose of tranexamic acid in oral combination drug formulation provided in the examples, below, are based on the MBL reduction targets established by the FDA[36] in the treatment of menorrhagia as well as the MBL-reducing potency of an NSAID selected for the inclusion in the combination drug formulation. The efficacy metrics reported for the oral tranexamic acid formulation (3900 mg daily dose, marketed in the US as Lysteda®) may serve as appropriate benchmarks.

Data from the Lysteda clinical program suggests 40% as a desirable treatment-induced decrease in the MBL in women with menorrhagia.[32] An approximate 40% decrease in MBL was also considered as clinically relevant in the scientific evaluation of oral tranexamic acid in the treatment of menorrhagia performed in 2000 by the European Agency for the Evaluation of Medicinal Products, EMEA. The same review indicated a dose-dependent increase in the efficacy of tranexamic acid.[34] A dose-dependent reduction in MBL is also evident from the Lysteda clinical study: the mean percent change in MBL for the 1950 mg/day regimen was approximately 25% vs. 39% for the 3900 mg/day dose.[36]

The data from the Lysteda clinical program also suggests 25% as an adequate treatment-induced decrease in the MBL in women with excessive MBL when pretreatment (baseline) MBL is relatively modest (less than 100 mL per menstrual cycle).[38] Such a decrease in MBL must be adequate for women with no clinical diagnosis related to menorrhagia.

The estimates below are based on data from individual clinical studies. Use of averages across all studies for any particular NSAID may also be considered. Alternatively, a specially designed study may be conducted to evaluate MBL reduction induced by an NSAID selected for the oral drug formulation in combination with tranexamic acid.

Example 1. One clinical study evaluated effect on MBL of 400 mg of ibuprofen administered four times daily. A 32% reduction in MBL was reported.[27,39] A complementary reduction of MBL (necessary to reach the 40% MBL reduction target in women clinically diagnosed with menorrhagia) would be 8%, or about one-third of the effect observed for the 1950 mg tranexamic acid daily dose as reported in the Lysteda label.[32] One-third of that dose (approximately 650 mg) would be an adequate daily supplement of tranexamic acid. The combined oral formulation would then consist of 400 mg of ibuprofen and 150-200 mg of tranexamic acid with a four times/day dosing schedule.

This oral combination drug formulation may be considered for women clinically diagnosed with primary or secondary dysmenorrhea and clinically diagnosed with menorrhagia.

Example 2. Another clinical study evaluated effect on MBL of 200 mg of ibuprofen administered three times daily. A 16% reduction in MBL was reported.[27,40] A complementary reduction of MBL (necessary to reach the 25% MBL reduction target in women with relatively modest baseline MBL) would be 8%, or about one-third of the effect observed for the 1950 mg tranexamic acid daily dose as reported in the Lysteda label.[32] One-third of that dose (approximately 650 mg) would be an adequate daily supplement of tranexamic acid. The combined oral formulation would then consist of 200 mg of ibuprofen and 200-250 mg of tranexamic acid with a three times/day dosing schedule.

This oral combination drug formulation may be considered for women with no clinical diagnosis related to dysmenorrhea and menorrhagia.

Example 3. Another clinical study evaluated effect on MBL of 50 mg of diclofenac sodium administered four times daily on Day 1 and three times on the following four days of the menstrual period. A 24% reduction in MBL was reported.[27,41] A complementary reduction of MBL (necessary to reach the 40% MBL reduction target in women clinically diagnosed with menorrhagia) would be 16%, or about two-thirds of the effect observed for the 1950 mg of tranexamic acid daily dose as reported in the Lysteda label.[32] Two-thirds of that dose (approximately 1300 mg) would be an adequate daily supplement of tranexamic acid. The combined oral formulation would then consist of 50 mg of diclofenac sodium and 325 mg of tranexamic acid with a four times/day dosing schedule.

This oral combination drug formulation may be considered for women clinically diagnosed with primary or secondary dysmenorrhea and clinically diagnosed with menorrhagia.

Example 4. Another clinical study evaluated effect on MBL of 500 mg of mefenamic acid administered three times daily during the menstrual period. A 30% reduction in MBL was reported for women clinically diagnosed with menorrhagia (baseline MBL>80 mL)[27,42] A complementary reduction of MBL (necessary to reach the 40% MBL reduction target in women clinically diagnosed with menorrhagia) would be 10%, or about two-fifths of the effect observed for the 1950 mg tranexamic acid daily dose as reported in the Lysteda label.[32] Two-fifths of that dose (approximately 800 mg) would be an adequate daily supplement of tranexamic acid. The combined oral formulation would then consist of 500 mg of mefenamic acid and 250-300 mg of tranexamic acid with a three times/day dosing schedule.

This oral combination drug formulation may be considered for women clinically diagnosed with primary or secondary dysmenorrhea and clinically diagnosed with menorrhagia.

Example 5. The study referenced in the previous example also evaluated the effect on MBL of 500 mg of mefenamic acid administered three times daily during the menstrual period in women with no clinical diagnosis of menorrhagia (baseline MBL<80 mL). A 19% reduction in MBL was reported.[27,42] A complementary reduction of MBL (necessary to reach the 25% MBL reduction target in women with relatively modest baseline MBL) would be 6%, or about one-fourth of the effect observed for the 1950 mg tranexamic acid daily dose as reported in the Lysteda label.[32] One-fourth of that dose (approximately 500 mg) would be an adequate daily supplement of tranexamic acid. The combined oral formulation would then consist of 500 mg of mefenamic acid and 150-200 mg of tranexamic acid with a three times/day dosing schedule.

This oral combination drug formulation may be considered for women with no clinical diagnosis related to dysmenorrhea and menorrhagia.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

REFERENCES

1. French Linda, M.D. American Family Physician, 2005 Jan. 15; 71(2): 285-291.
2. MerckMedicus Modules: Dysmenorrhea—Epidemiology; accessed on Jul. 25, 2010 at http://www.merckmedicus.com/pp/us/hcp/diseasemodules/dysmenorrhea/epidemiology.jsp (reference on file)
3. Heavy menstrual bleeding: Assessing Impact, Evaluating Management Options; Supplement to OBG Management, October 2009; accessed at http://www.obgmanagement.com/PDF/supplOBG_heavybleeding.pdf (reference on file)
4. David Chelmow Non-surgical Options for Menorrhagia. OBG Management November 2005 (Vol. 17, No. 11)
5. Andrew M. Kaunitz Modern Management of Heavy Menstrual Bleeding (presentation on file)
6. National Collaborating Centre for Women's and Children's Health. Heavy menstrual bleeding. London (UK): Royal College of Obstetricians and Gynaecologists (RCOG); 2007 January.
7. Barbara S, Apgar et al. Treatment of Menorrhagia. American Family Physician—Volume 75, Issue 12 (June 2007)
8. Coco A S. MD. Primary dysmenorrhea. *American Family Physician* 1999; 60: 489-496.
9. Proctor M, Farquhar C. Dysmenorrhoea. In: *Clinical evidence*. Issue 11. London: BMJ Publishing, 2004.
10. Ronald T. Burkman, MD; Sandra A. Carson, MD Non-contraceptive Health Benefits of Progestin-Only Contraceptive Agents The Female Patient|Vol 33 August 2008
11. Dawood, Y, *Glob. libr. women's med.*, (*ISSN:* 1756-2228) 2008; DOI 10.3843/GLOWM.10009a, Dysmenorrhea The Global Library of Women's Medicine, 2008; accessed at http://www.glowm.com/index.html?p=glowm.cml/section_view&articleid=9 (reference on file)
12. RECOMMENDATIONS FOR THE TREATMENT OF DYSMENORRHEA. 2000. University of Texas at Austin School of Nursing, Family Nurse Practitioner Program.
13. ACOG Practice Bulletin No. 51. Chronic pelvic pain. Obstet Gynecol. 2004 March; 103(3):589-605.
14. Primary Dysmenorrhea Consensus Guideline Society of Obstetricians and Gynaecologists of Canada, No 169, December 2005.
15. Marjoribanks J, Proctor M L, Farquhar C. Nonsteroidal anti-inflammatory drugs for primary dysmenorrhoea. In: The Cochrane Library, Issue 2, 2006.
16. Zhang W Y, Li Wan Po A. Efficacy of minor analgesics in primary dysmenorrhoea: a systematic review. *Br J Obstet Gynaecol* 1998; 105:780-789.
17. Ponstel®. Full Prescribing Information.
18. Motrin®. Full Prescribing Information.
19. Ibuprofen Oral: Dosage, Uses and Warnings
20. Cataflam®) Full Prescribing Information.
21. Naproxen Sodium. Full Prescribing Information.
22. Ketoprofen Full Prescribing Information.
23. Meclofenamate sodium. Full Prescribing Information.
24. Oeller M K, Rees M C P. Menorrhagia: an update. Acta Obstet Gynecol Scand 2003; 82: 405-422
25. Duckitt K., Collins S. Menorrhqagia. Clinical Evidence BMJ publishing group 2008.
26. Lethaby A, et al. *Cochrane Database Syst Rev.* 2007; (4):CD000400.
27. Working Party for Guidelines for the Management of Heavy Menstrual Bleeding. An evidence-based guideline for the management of heavy menstrual bleeding. New Zealand Medical Journal. 1999; 112: 174-177
28. Joseph Y. Lee, et al. Treatment of Menorrhagia with Tranexamic Acid. J Soc Obstet Gynaecol Can 2000; 22(10):794-8
29. International Women's Health Update Management Options Antifibrinolytics; Monash University
30. Bonnar J, Sheppard B L. Treatment of menorrhagia during menstruation: randomised controlled trial of ethamsylate, mefenamic acid, and tranexamic acid. *BMJ.* 1996; 313 (7057): 579-582.
31. Clinical Data Demonstrates That LYSTEDA™ Significantly Reduced Menstrual Blood Loss and Limitations on Social, Leisure and Physical Activities in Women With Cyclic HMB; May 19, 2010/PRNewswire/; accessed at http://www.prnewswire.com/news-releases/clinical-data-demonstrates-that-lysteda-significantly-reduced-menstrual-blood-loss-and-limitations-on-social-leisure-and-physical-activities-in-women-with-cyclic-hmb-94244299.html (reference on file)
32. Lysteda®. Full Prescribing Information.
33. Cyklokapron®. Summary of Product Characteristics
34. Overall Summary of the Scientific Evaluation of Cycle-f, EMEA, 2000
35. Mohri H. High dose of tranexamic acid for treatment of severe menorrhagia in patients with von Willebrand disease. *J Thromb Thrombolysis.* 2002 December; 14(3): 255-7.
36. LCenter for Drug Evaluation and Research. Application Number 22-430. Lysteda® NDA Medical review; accessed at http://www.accessdata.fda.gov/drugsatfda_docs/nda/2009/022430s000medr.pdf (reference on file)
37. Sanfilippo J S. Nonresectoscopic endometrial ablation devices. OBG Management. 2009; December: S4-S5 (suppl).
38. Muse K N., et al. Effect of Baseline Menstrual Blood Loss or Body Mass Index on Menorrhagia Treated with a Novel Tranexamic Acid. ACOG 58th Annual Clinical Meeting San Francisco, Calif. May 15-May 19, 2010. Poster presentation: published abstract online at http://www.acog.org/acm/pdf/postersMon.pdf (reference on file)
39. Roy S, Shaw S T Jr. Role of prostaglandins in IUD-associated uterine bleeding—effect of a prostaglandin synthetase inhibitor (ibuprofen). Obstet Gynecol 1981; 58: 101-6.
40. Makarainen L, Ylikorkala O. Primary and myoma-associated menorrhagia: role of prostaglandins and effects of ibuprofen. Br J Obstet Gynaecol 1986; 93: 974-978.
41. Ylikorkala O, Viinikka L. Comparison between antifibrinolytic and antiprostaglandin treatment in the reduction of increased menstrual blood loss in women with intrauterine contraceptive devices. Br J Obstet Gynaecol 1983; 90 (1): 78-83.
42. Fraser I S, Pearse C, Shearman R P, Elliott P M et al. Efficacy of mefenamic acid in patients with a complaint of menorrhagia. Obstet Gynecol 1981; 58: 543-551.
43. Caraceni A. et al., Pain Measurement Tools and Methods in Clinical Research. Journal of Pain and Symptom Management, Vol. 23 No. 3 March 2002

What is claimed is:

1. A method for relieving menstrual pain and reducing menstrual blood loss in a female comprising:
   administering to the female an oral combination drug formulation comprising a first therapeutically effective dose of a non-steroidal anti-inflammatory drug (NSAID) and a second complementary low dose of tranexamic acid, wherein the NSAID is formulated to relieve the menstrual pain and to reduce a volume of menstrual blood loss of the female, wherein the dose of tranexamic acid ranges from 50 mg to 150 mg per the oral combination drug formulation; wherein a total daily dose of the tranexamic acid ranges from 390 mg to 500 mg.

2. The method of claim 1, wherein the oral combination drug formulation is in a form of any one of: an oral tablet, an oral capsule, and an oral caplet.

3. The method of claim 2, wherein the NSAID comprises any one of: ibuprofen, naproxen, diclofenac, ketoprofen, mefenamic acid, and metabolites thereof.

4. The method of claim 3, wherein the dose of the NSAID per oral combination drug formulation ranges from 5 mg to 1000 mg.

5. The method of claim 4, wherein the dose of the NSAID per oral combination is any one of: from 100 mg to 800 mg of the ibuprofen, from 150 mg to 600 mg of the naproxen, from 5 mg to 50 mg of the diclofenac, from 5 mg to 50 mg of the ketoprofen, and from 50 mg to 500 mg of the mefenamic acid.

6. The method of claim 1, wherein the female has a condition that comprises any one of: primary dysmenorrhea, secondary dysmenorrhea, menorrhagia, idiopathic menorrhagia, cyclic heavy menstrual bleeding, dysfunctional uterine bleeding, anemia, menstrual bleeding of less than 80 ml per menstrual cycle, and menstrual bleeding of more than 80 ml per menstrual cycle.

7. The method of claim 1, wherein the oral combination drug formulation is administered: from the onset of menstrual bleeding until the resolution of related symptoms; from the onset of menstrual bleeding until the end of the menstrual period.

8. A method for relieving menstrual pain and reducing menstrual blood loss in a female comprising:
administering to the female an oral combination drug formulation comprising a first therapeutically effective dose of a non-steroidal anti-inflammatory drug (NSAID) and a second complementary low dose of tranexamic acid, wherein the NSAID is formulated to relieve the menstrual pain and to reduce a volume of the menstrual blood loss, wherein a total daily dose and a dose per oral combination drug formulation of tranexamic acid is selected based on a contribution of the NSAID to the reduction of menstrual blood loss and wherein the dose of the tranexamic acid per the oral combination drug formulation ranges from 50 mg to 150 mg; wherein a total daily dose of the tranexamic acid ranges from 390 mg to 500 mg.

9. The method of claim 8, wherein the NSAID has any one of: proven analgesic efficacy and an indication for the treatment of menstrual pain.

10. The method of claim 8, wherein the NSAID comprises any one of: ibuprofen, naproxen, diclofenac, ketoprofen, mefenamic acid, and metabolites thereof.

11. The method of claim 8, wherein the dose of the tranexamic acid per oral combination drug formulation is any one of: from 50 mg to 100 mg, and from 100 mg to 150 mg.

12. The method of claim 10, wherein the oral combination drug formulation comprises 400 mg of the ibuprofen and 100 mg of the tranexamic acid, wherein the oral combination drug formulation is administered four times daily.

13. The method of claim 10, wherein the oral combination drug formulation comprises 200 mg of the ibuprofen and 125 mg of the tranexamic acid, wherein the oral combination drug formulation is administered four times daily.

* * * * *